(12) United States Patent
Mendes et al.

(10) Patent No.: US 8,017,803 B2
(45) Date of Patent: Sep. 13, 2011

(54) PROCESS FOR THE PREPARATION OF TAMSULOSIN AND INTERMEDIATES THEREOF

(75) Inventors: Zita Mendes, Lisboa (PT); Joana Baptista, Lisbon (PT); Dionisio Martin, Salamanca (ES); William Heggie, Palmela (PT)

(73) Assignee: Hovione Inter Ltd., Lucerne (CH)

( * ) Notice: Subject to any disclaimer, the term of this patent is extended or adjusted under 35 U.S.C. 154(b) by 900 days.

(21) Appl. No.: 11/721,028

(22) PCT Filed: Jan. 18, 2005

(86) PCT No.: PCT/GB2005/000155
§ 371 (c)(1),
(2), (4) Date: Dec. 10, 2007

(87) PCT Pub. No.: WO2006/061549
PCT Pub. Date: Jun. 15, 2006

(65) Prior Publication Data
US 2009/0234154 A1    Sep. 17, 2009

(30) Foreign Application Priority Data

Dec. 6, 2004  (PT) .......................... 103.216

(51) Int. Cl.
*C07C 311/39* (2006.01)
*C07C 311/40* (2006.01)
(52) U.S. Cl. .......................................... 564/86
(58) Field of Classification Search .............. 564/86
See application file for complete search history.

(56) References Cited

U.S. PATENT DOCUMENTS

| | | | |
|---|---|---|---|
| 4,000,197 | A | 12/1976 | Barfknecht et al. |
| 4,373,106 | A | 2/1983 | Imai et al. |
| 4,731,478 | A | 3/1988 | Niigata et al. |
| 4,761,500 | A | 8/1988 | Niigata et al. |
| 5,447,958 | A | 9/1995 | Niigata et al. |
| 7,105,698 | B2 | 9/2006 | Blanco Fernandez et al. |
| 2007/0106079 | A1 | 5/2007 | Dambrin et al. |

FOREIGN PATENT DOCUMENTS

| | | |
|---|---|---|
| EP | 0034432 A2 | 8/1981 |
| EP | 0034432 B1 | 4/1984 |
| EP | 0257787 A1 | 3/1988 |
| EP | 0380144 A1 | 8/1990 |
| FR | 2864079 | 6/2005 |
| JP | 58013669 | 1/1983 |
| WO | 02068382 A1 | 9/2002 |
| WO | 03035608 A1 | 5/2003 |
| WO | 03037850 A1 | 5/2003 |
| WO | 2004006829 | 1/2004 |
| WO | 2004087623 A2 | 10/2004 |
| WO | 2006061549 A1 | 6/2006 |

OTHER PUBLICATIONS

Foreign communication from the priority application—International Preliminary Report on Patentability, PCT/GB2005/000155, Jun. 13, 2007, 6 pages.
Foreign communication from a related counterpart application—International Search Report and Written Opinion, PCT/GB2005/000155, Aug. 22, 2005, 9 pgs.

*Primary Examiner* — Peter O Sullivan
(74) *Attorney, Agent, or Firm* — Conley Rose, P.C.; Rodney B. Carroll

(57) ABSTRACT

A process for producing tamsulosin of formula I

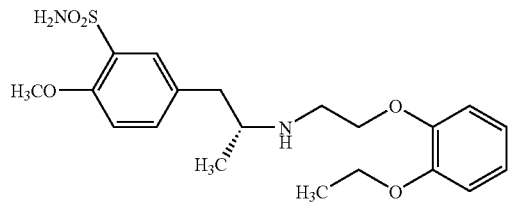

and pharmaceutically acceptable addition salts, thereof comprises the steps of:
a) Reacting compound R,R-[2-(4-methoxy-phenyl)-1-methyl-ethyl]-(1-phenyl-ethyl)-amine of formula II or a salt thereof

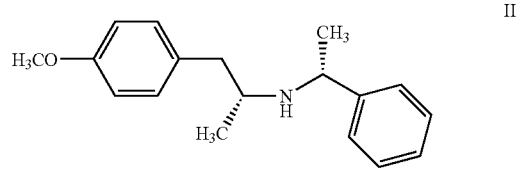

with chlorosulfonic acid with or without an organic solvent, to obtain compound R,R-2-methoxy-5-[2-(1-phenyl-ethylamino)-propyl]-benzenesulfonic acid of formula III

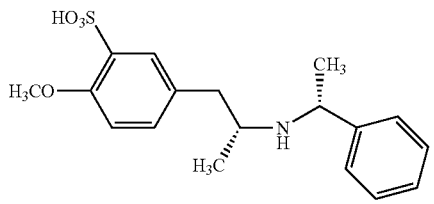

b) Hydrogenolysis of compound R,R-2-methoxy-5-[2-(1-phenyl-ethylamino)-propyl]-benzenesulfonic acid of formula III or a salt thereof carried out in an alcohol in the presence of a palladium catalyst using hydrogen or a source of hydrogen, to obtain compound R-(−)-5-(2-amino-propyl)-2-methoxy-benzenesulfonic acid of formula IV

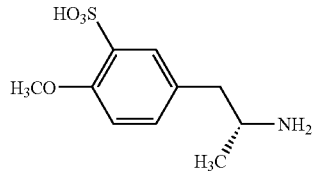

IV c) Reacting primary amine R-(−)-5-(2-amino-propyl)-2-methoxy-benzenesulfonic acid of formula IV, or a salt thereof, with a compound of formula V

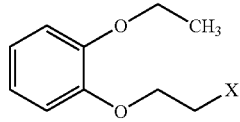

V wherein X represents an halogen atom selected from the group consisting of Cl; Br and I, to obtain 5-{(2R)-2-[2-(2-ethoxy-phenoxy)-ethylamino]-propyl}-2-methoxy-benzenesulfonic acid compound of formula VI

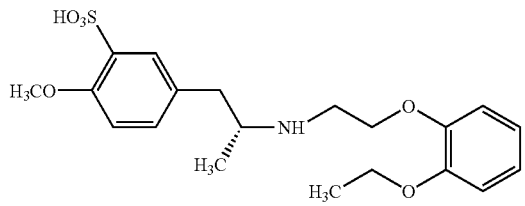

VI d) Reacting compound of formula VI with an halogenating agent, to obtain the corresponding sulfonylchloride of formula VII.

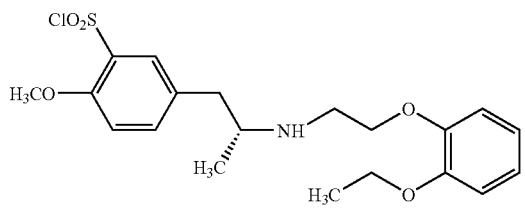

VII e) Reacting compound VII with ammonia to obtain compound I.

22 Claims, No Drawings

PROCESS FOR THE PREPARATION OF TAMSULOSIN AND INTERMEDIATES THEREOF

CROSS-REFERENCE TO RELATED APPLICATIONS

This application is a filing under 35 U.S.C. 371 of International Application No. PCT/GB2005/000155 filed Jan. 18, 2005, entitled "Process for the Preparation of Tamsulosin and Intermediates Thereof," claiming priority of Portuguese Patent Application No. 103.216 filed Dec. 6, 2004, which applications are incorporated by reference herein in their entirety.

FIELD OF THE INVENTION

The present invention relates to a process for preparing tamsulosin (compound I) and its pharmaceutically acceptable addition salts, such as the hydrochloride; and to new intermediate compounds.

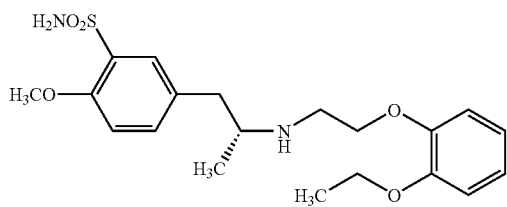

This invention relates to a convenient and improved process for the preparation of 5-{(2R)-2-[2-(2-ethoxy-phenoxy)-ethylamino]-propyl}-2-methoxy-benzenesulfonamide known as tamsulosin, of formula I, and pharmaceutical acceptable addition salts thereof.

The present invention also relates to improved and convenient processes for the preparation of four new compounds of formulas III, IV, VI and VIII.

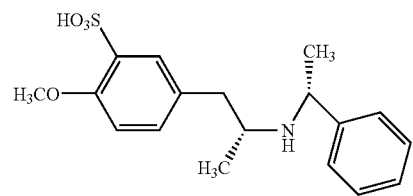

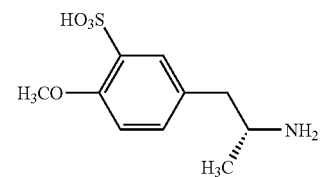

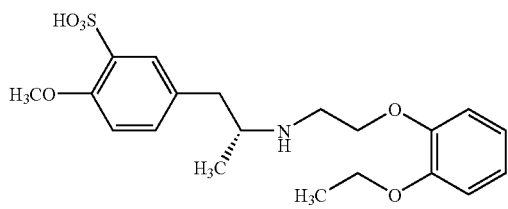

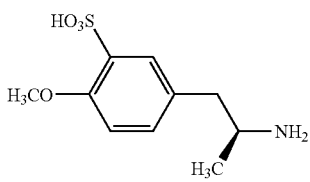

BACKGROUND OF THE INVENTION

Tamsulosin hydrochloride is a selective $\alpha_1$ adrenergic antagonist that has been shown to improve symptoms and urinary flow rate in patients with benign prostatic hyperplasia (BPH).

Commercially marketed product is a hydrochloride salt of the (R) enantiomer of tamsulosin.

EP034432 and U.S. Pat. No. 4,373,106 disclose the preparation of racemic tamsulosin by two processes:

1) "Process A" comprises the condensation of the ketone of formula A with the amine of formula B followed by reduction of the intermediate Schiff base formed.

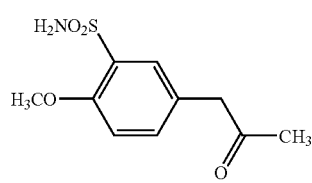

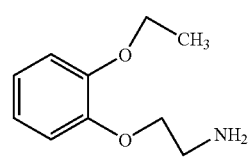

2) "Process B" describes a process that goes through a hydroxyl and a chloro-analogue intermediates followed by reduction of the chloro analogue intermediate, according to the following sequence:

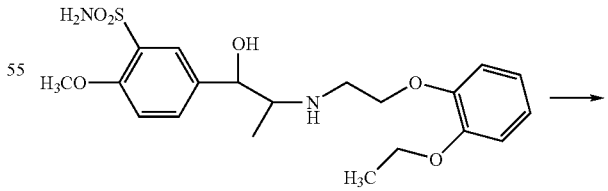

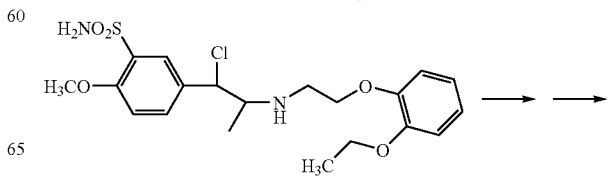

-continued

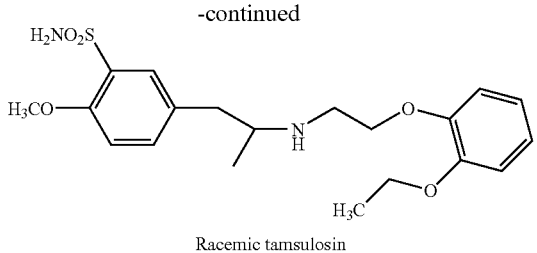

Racemic tamsulosin

The above processes have the disadvantage that they need further resolution of the racemic product to obtain the desired more active R(−) tamsulosin. Processes for this difficult resolution of the racemic mixture are described, for example, in Japanese Patent Application No. JP-56-110665, in WO03/037850 and in WO2004/006829.

U.S. Pat. No. 4,731,478, U.S. Pat. No. 4,761,500 and U.S. Pat. No. 5,447,958 in addition to the two processes above mentioned for the preparation of racemic tamsulosin disclose a process for the preparation of both optically pure enantiomers of tamsulosin.

The process comprises the preparation of any of the two optically pure 5-(2-amino-propyl)-2-methoxy-benzene-sulphonamide enantiomers followed by reaction with 2-(o-ethoxy-phenoxy)ethyl bromide compound of formula D to form the corresponding (R) and (S) tamsulosin. The process for the preparation of the R(−) tamsulosin isomer is illustrated in the following scheme:

This process has the disadvantage that the starting compound (2R)-2-(4-methoxy-phenyl)-1-methyl-ethylamine is a known hallucinogenic substance, handling of which is undesirable.

EP257787 and its divisional EP380144 disclose:

1) An alternative process for the preparation, among others, of the pure optically amine of formula C

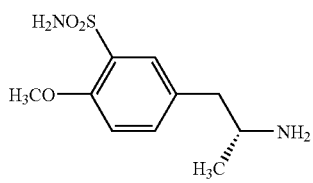

according to the following scheme:

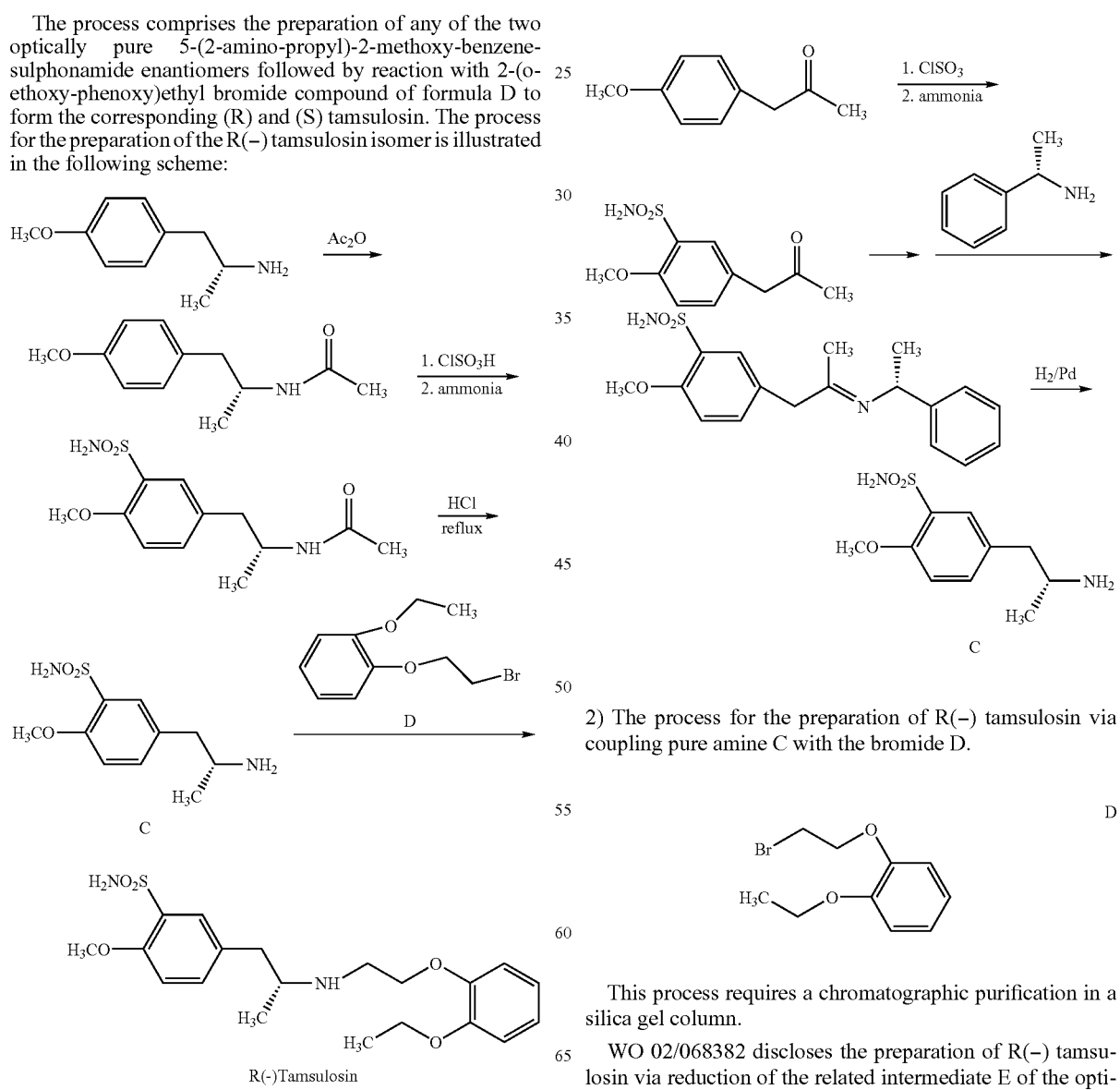

2) The process for the preparation of R(−) tamsulosin via coupling pure amine C with the bromide D.

This process requires a chromatographic purification in a silica gel column.

WO 02/068382 discloses the preparation of R(−) tamsulosin via reduction of the related intermediate E of the optically pure amine C, according to the following scheme.

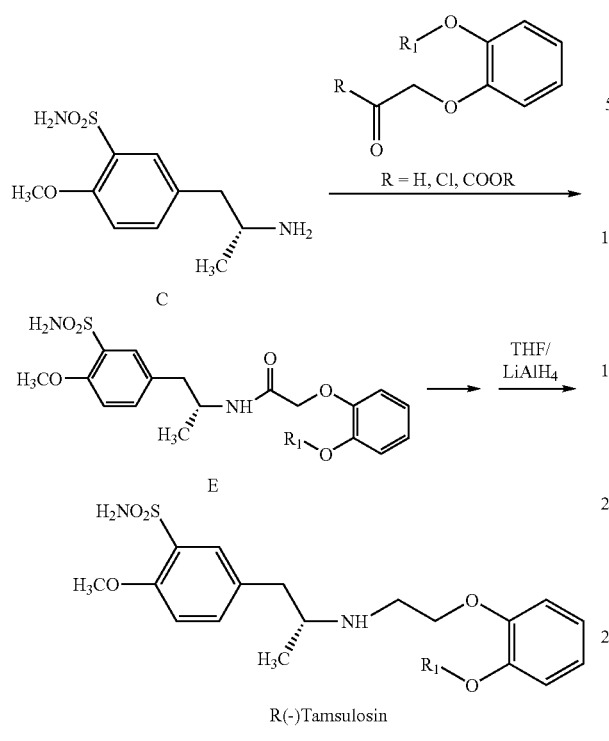

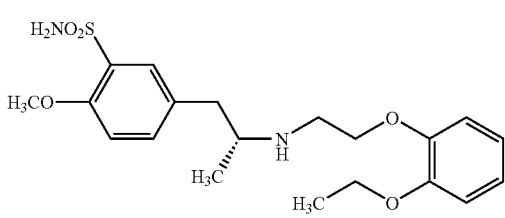

R(-)Tamsulosin

We have now devised an improved process for the preparation of tamsulosin, which process overcomes or substantially minimises the problems associated with the prior art processes.

SUMMARY OF THE INVENTION

According to the present invention, there is provided a process for producing 5-{(2R)-2-[2-(2-ethoxy-phenoxy)-ethylamino]-propyl}-2-methoxy-benzenesulfonamide of formula I

I

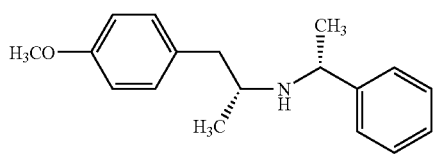

and pharmaceutically acceptable addition salts thereof, which process comprises the steps:

Step a) Reacting compound R,R-[2-(4-methoxy-phenyl)-1-methyl-ethyl]-(1-phenyl-ethyl)-amine of formula II or a salt thereof

II

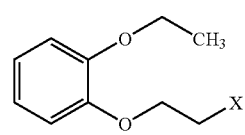

with chlorosulfonic acid with or without an organic solvent, to obtain compound R,R-2-methoxy-5-[2-(1-phenyl-ethylamino)-propyl]-benzenesulfonic acid of formula III

III

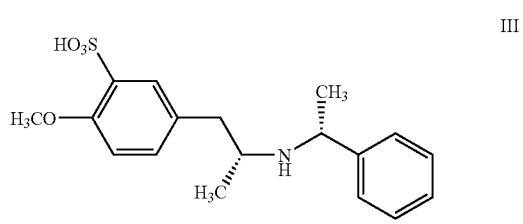

Step b) Hydrogenolysis of compound R,R-2-methoxy-5-[2-(1-phenyl-ethylamino)-propyl]-benzenesulfonic acid of formula III or a salt thereof carried out in an alcohol in the presence of a palladium catalyst using hydrogen or a source of hydrogen, to obtain compound R-(−)-5-(2-amino-propyl)-2-methoxy-benzenesulfonic acid of formula IV

IV

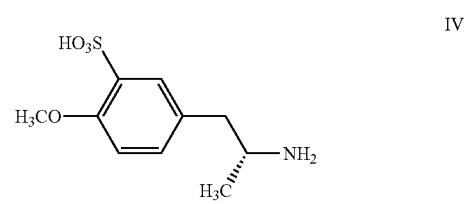

Step c) Reacting primary amine R-(−)-5-(2-amino-propyl)-2-methoxy-benzenesulfonic acid of formula IV, or a salt thereof, with a compound of formula V

V

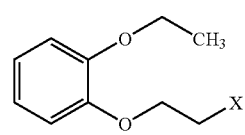

wherein X represents an halogen atom selected from the group consisting of Cl; Br and I, to obtain 5-{(2R)-2-[2-(2-ethoxy-phenoxy)-ethylamino]-propyl}-2-methoxy-benzenesulfonic acid compound of formula VI

VI

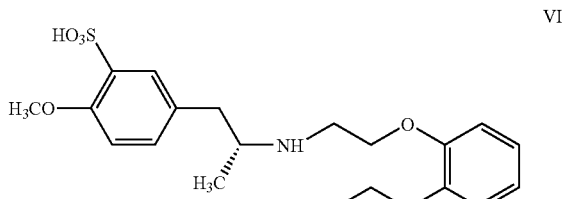

Step d) Reacting compound of formula VI with a halogenating agent, to obtain the corresponding sulfonylchloride of formula VII

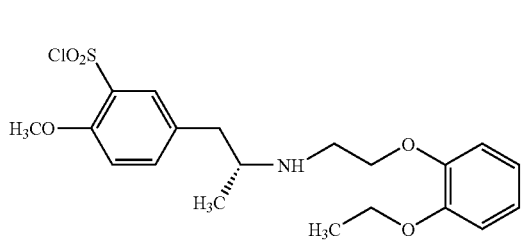

VII

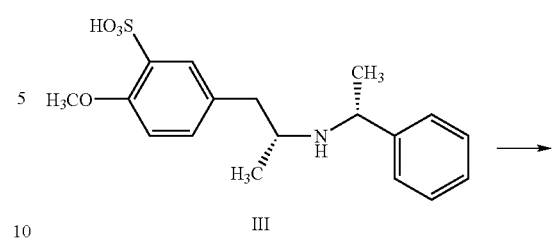

III

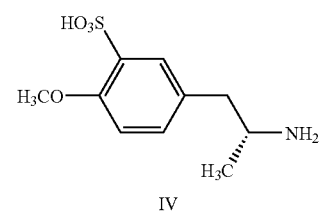

IV

Step e) Reacting compound of formula VII with ammonia to obtain compound I.

The invention also provides the intermediate compounds R,R-2-methoxy-5-[2-(1-phenyl-ethylamino)-propyl]-benzenesulfonic acid of formula III; R-(−)-5-(2-amino-propyl)-2-methoxy-benzenesulfonic acid of formula IV; 5-{(2R)-2-[2-(2-ethoxy-phenoxy)ethylamino]-propyl}-2-methoxy-benzenesulfonic acid of formula VI; S-(+)-5-(2-amino-propyl)-2-methoxy-benzenesulfonic acid of formula VIII.

In a further aspect, the invention provides the use of the above intermediate compounds for preparing tamsulosin or a pharmaceutically acceptable addition salt thereof.

Also provided is a pharmaceutical composition comprising tamsulosin or a pharmaceutically acceptable addition salt thereof made according to the process of the invention and a pharmaceutically acceptable carrier or excipient.

The invention also provides processes for making the new intermediate compounds of the invention, of formulas III, IV, VI and VIII, as defined below.

DETAILED DESCRIPTION

Compounds of formulas III, IV and VI are key intermediates for the preparation of compound I.

Compound III can be prepared by reacting compound R,R-[2-(4-methoxy-phenyl)-1-methyl-ethyl]-(1-phenyl-ethyl)-amine of formula II or a salt thereof with an excess of chlorosulfonic acid with or without a solvent.

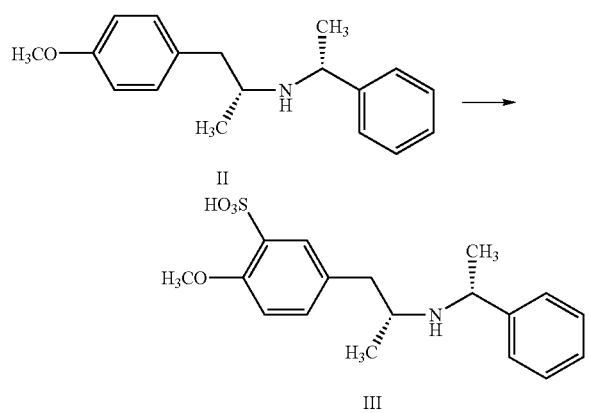

Compound IV can be prepared by hydrogenolysis of compound R,R-2-methoxy-5-[2-(1-phenyl-ethylamino)-propyl]-benzenesulfonic acid of formula III or a salt thereof in the presence of a palladium catalyst using hydrogen or a source of hydrogen.

Compound VI can be prepared by condensing compound R-(−)-5-(2-amino-propyl)-2-methoxy-benzenesulfonic acid formula IV with an halide compound of formula V

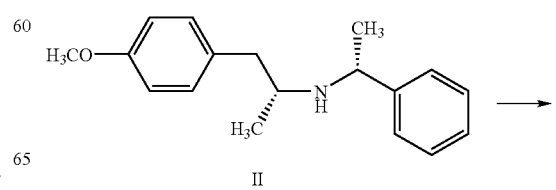

wherein X represents a halogen atom selected from the group consisting of Cl, Br and I.

Step (a) preferably comprises reacting compound R,R-[2-(4-methoxy-phenyl)-1-methyl-ethyl]-(1-phenyl-ethyl)-amine of formula II or a salt thereof, with an excess of chlorosulfonic acid with or without an organic solvent at a temperature from −30° C. to 10° C. to obtain the new compound R,R-2-methoxy-5-[2-(1-phenyl-ethylamino)-propyl]-benzenesulfonic acid of formula III.

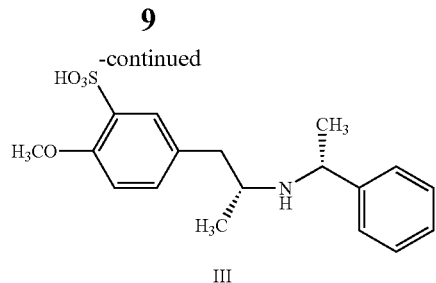

III

For step (a), suitable organic solvents include dichloromethane, monochlorobenzene and 1,2-dichloroethane.

Preferred reaction conditions for step (a) include (i) carrying out the reaction with an excess from 2.0 to 3.5 equivalents of chlorosulfonic acid (ii) using dichloromethane and (iii) using a temperature from −10° C. to 10° C. Preferably, all three features are employed.

The preparation of the starting compound R,R-[2-(4-methoxy-phenyl)-1-methyl-ethyl]-(1-phenyl-ethyl)-amine of formula II, is disclosed in U.S. Pat. No. 4,000,197.

Another embodiment of the present invention is providing an improved and simplified process for the preparation of the starting compound of formula II, which process comprises reacting under mild conditions, p-methoxyphenyl acetone with R-(+)-1-phenyl ethyl amine in an organic solvent, such as methanol or ethanol in the presence of hydrogen and a platinum catalyst.

The compound of formula II can be isolated as an addition salt with inorganic or organic acid and is recrystallized in order to achieve the chiral purity required, preferably from acetone or a mixture of acetone and methyl-tert-butyl-ether (MTBE). A particularly convenient salt of compound II is the hydrochloride salt.

Step (b) preferably comprises hydrogenolysis of compound R, R-2-methoxy-5-[2-(1-phenyl-ethylamino)-propyl]-benzenesulfonic acid of formula III or a salt thereof in a lower alcohol of 1-3 carbon atoms at a temperature from 30° C. to 65° C. in the presence of a palladium catalyst using hydrogen or a source of hydrogen, to yield R-(−)-5-(2-aminopropyl)-2-methoxy-benzenesulfonic acid of formula IV.

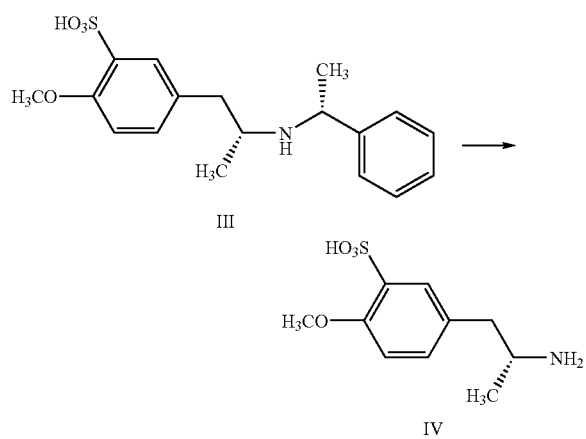

In step (b), suitable sources of hydrogen include: ammonium formate, cyclohexene or sodium tetrahydroborate, preferably ammonium formate.

Suitable solvents include methanol, ethanol, isopropanol or a mixture of two or more thereof, preferably methanol or ethanol.

Palladium catalysts include Pd/C, preferably Pd/C 5%.

The reaction is suitably carried out at a temperature of from 30° C. to 65° C., preferably from 50° C. to 60° C.

Crystallization of the crude product, for example from ethanol, yields the required purity of compound IV.

The hydrogenolysis conditions of the present invention provide a clean and fast reaction to produce the new compound IV.

Step (c) preferably comprises condensation of compound R-(−)-5-(2-amino-propyl)-2-methoxy-benzenesulfonic acid of formula IV with 2-(o-ethoxyphenoxy)-ethyl halide of formula V in which X represents an halogen atom selected from the group consisting of Cl; Br and I, in an organic solvent, at a temperature from 25° C. to 110° C., in the presence of a base to obtain 5-{(2R)-2-[2-(2-ethoxy-phenoxy)ethylamino]-propyl}-2-methoxy-benzenesulfonic acid of formula VI.

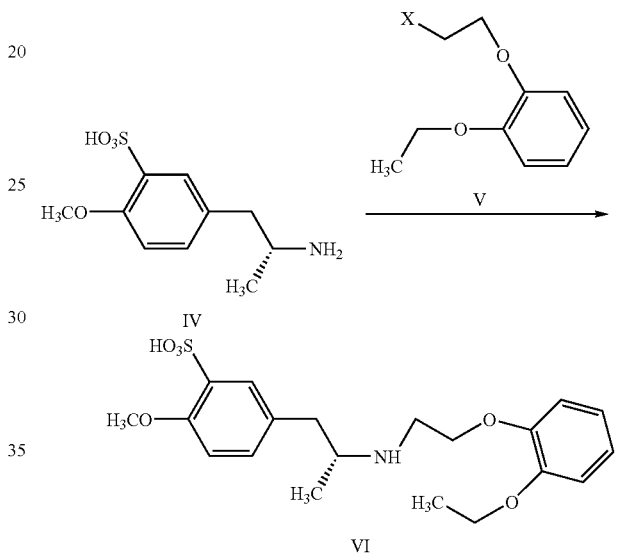

Suitable solvents for step (c) of the present invention include ethanol, dimethylformamide and water or a mixture thereof, preferably a mixture of dimethylformamide and water.

The compound IV is preferably used in a slight molar excess of from 1.0 to 1.2 moles per mole of halide compound V. Preferably, this is carried out in the presence of an excess of a carbonate or a hydrogen carbonate of an alkali metal.

The preferred base is potassium carbonate and the preferred molar ratio is 4.5 to 5.0 moles of potassium carbonate per mole of halide compound V.

The reaction is suitably carried out at a temperature of from 25° C. to 110° C., preferably from 75° C. to 90° C.

The conditions of step (c) according to the present invention have the following advantages: practically no molar excess of the expensive amine of formula IV is necessary to complete the condensation; in addition, in contrast to the prior art the use of column chromatography is not necessary to purify the product.

Step (d) preferably comprises reacting compound 5-{(2R)-2-[2-(2-ethoxy-phenoxy)-ethylamino]-propyl}-2-methoxy-benzenesulfonic acid of formula VI with a halogenating agent, in an organic solvent at a temperature from −30° C. to 0° C. to obtain the corresponding sulfonylchloride, a new compound of formula VII.

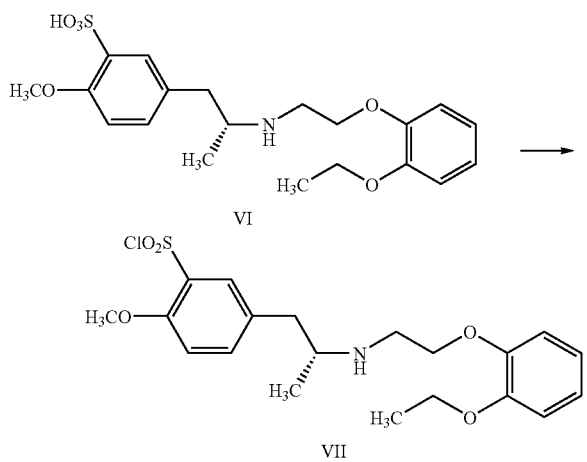

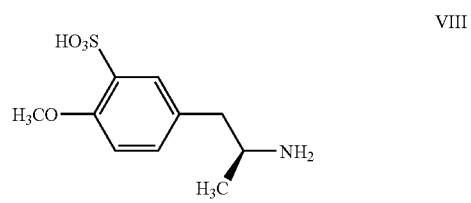

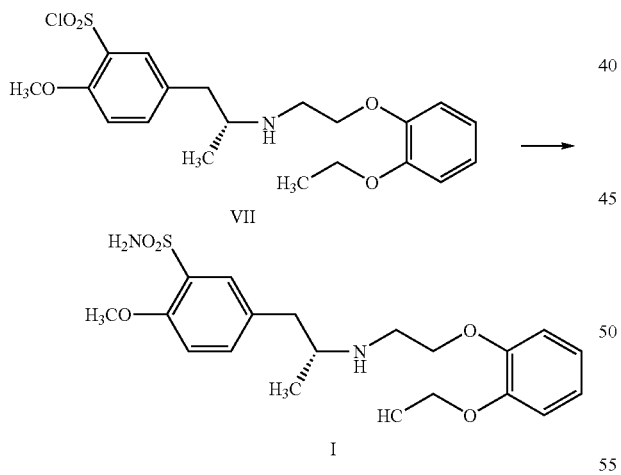

The preferred halogenating agent is thionyl chloride.

The halogenating agent can be used as solvent, but the preferred conditions of the present invention are using thionyl chloride in a slight excess in an organic solvent. This affords a cleaner reaction in addition to being safer and more environmentally friendly.

Preferred organic solvents for the reaction include dimethylformamide and dichloromethane, most preferably a mixture of dimethylformamide and dichloromethane.

The reaction can suitably be carried out at from −30° C. to 0° C., but most preferably the halogenation reaction of the invention is carried out at from −5° C. to 0° C.

Step (e) preferably comprises reacting the sulfonyl chloride compound of formula VII with ammonia in an organic solvent, at a temperature from 0° to 30° C. to obtain tamsulosin, compound of formula I.

The preferred organic solvent for step (e) of the present invention is tetrahydrofuran.

The reaction is preferably carried out at a temperature from 0° C. to 30° C., more preferably at from 15° C. to 25° C.

The tamsulosin base obtained can, for example, be converted into its hydrochloride salt by adding an ethanolic hydrochloric acid solution to the tamsulosin base solution in ethanol.

Another embodiment of the invention is the preparation of the new compound S-(+)-5-(2-amino-propyl)-2-methoxy-benzenesulfonic acid formula VIII or an addition salt thereof, Compound VIII can, for example, be prepared by following the same procedure described above to prepare compound R-(−)-5-(2-amino-propyl)-2-methoxy-benzenesulfonic acid of formula IV, but starting from p-methoxyphenylacetone and S-(−)-phenyl ethylamine instead of R-(+)-phenyl ethylamine.

Acid addition salts of compounds II, III, IV, VI, VII and VIII may be prepared by methods known in the art. For example, the base is reacted with an excess of acid in a water miscible solvent such as ethanol, methanol or acetone.

EXAMPLES

The following examples serve to illustrate the present invention and certain preferred embodiments thereof.

Example 1

R,R-[2-(4-methoxy-phenyl)-1-methyl-ethyl]-(1-phenyl-ethyl)-amine (formula II)

To a methanol solution of p-methoxyphenylacetone (34 g, 0.207 mol) was added R-(+)-phenyl ethylamine (26.1 ml, 0.205 mol). The solution was stirred until homogeneous and then there was added 0.75 g of a platinum oxide catalyst.

The mixture was hydrogenated at a pressure of 2 bar and at a temperature of 50° C. for 12 hours. At the end of this period, the catalyst was filtered and the filtrate evaporated until oil was obtained.

To this oil, 119 ml of ethanolic hydrogen chloride was added, and the mixture stirred for 3 hours at room temperature.

Ethanol was evaporated and to the oil obtained was added 300 ml of a mixture of acetone:MTBE (9:4) v/v.

The solid was filtered, washed with acetone, and dried, yielding 30 g of R,R-[2-(4-methoxy-phenyl)-1-methyl-ethyl]-(1-phenyl-ethyl)-amine hydrochloride after crystallization and with a purity of 96.2% in area by HPLC.

Example 2

R,R-2-methoxy-5-[2-(1-phenyl-ethylamino)-propyl]-benzenesulfonic acid (formula III)

To a suspension of R,R-[2-(4-methoxy-phenyl)-1-methyl-ethyl]-(1-phenyl-ethyl)-amine hydrochloride (21 g, 0.0688 mol) in dichloromethane, cooled at 5° C., was added drop wise chlorosulfonic acid (14.7 ml, 0.22 mol).

The resulting solution was stirred at −5° C./5° C. for 2 hours. At the end of this period 56 ml of ethanol was added to destroy the excess of chlorosulfonic acid maintaining the temperature at −5° C./5° C.

Dichloromethane was removed by evaporation under vacuum.

The reaction mixture is poured into 500 ml of water. The product precipitates and is filtered and washed with water and dried, yielding 23 g of the title compound with a purity of 95% in area determined by HPLC.

Example 3

R-(−)-5-(2-amino-propyl)-2-methoxy-benzene-sulfonic acid (formula IV)

To a suspension of R,R-2-methoxy-5-[2-(1-phenyl-ethylamino)-propyl]-benzenesulfonic acid (20 g, 0.0572 mol) in methanol was added, carefully, 20 g of wet 5% Pd/C (0.5 g Pd), and ammonium formate (18 g, 0.285 mol).

The resulting mixture was stirred at 50° C./60° C.

When reaction is completed water (110 ml) was added and reaction mixture is stirred 1 hour at room temperature.

The catalyst was filtered off and the filtrate evaporated until oil was obtained.

The product is crystallized from ethanol, filtered and dried, yielding 13.2 g of the title compound with a purity of 97% in area, by HPLC.

Example 4

5-{(2R)-2-[2-(2-ethoxy-phenoxy)ethylamino]-propyl}-2-methoxy-benzenesulfonic acid (formula VI)

To a suspension of R-(−)-5-(2-amino-propyl)-2-methoxy-benzenesulfonic acid (10 g, mol) in dimethylformamide and water at 95° C./100° C. was added 2-(O-ethoxy-phenoxy)ethylbromide (10 g, 0.0408 mol) and potassium carbonate (25 g, 0.1809 mol).

The resulting mixture was stirred at 95° C./100° C. until reaction is completed.

When reaction is completed the suspension is filtered off and to the filtrate 38 ml of ethanolic hydrogen chloride was added. The mixture stirred for 1 hour at room temperature.

After this agitation time 90 ml of MTBE was added.

The solid was filtered, washed with MTBE, dried, yielding 13.7 g of 5-{(2R)-2-[2-(2-ethoxy-phenoxy)ethylamino]-propyl}-2-methoxy-benzenesulfonic acid hydrochloride with a purity of 97.9% in area by HPLC.

Example 5

5-{(2R)-2-[2-(2-ethoxy-phenoxy)-ethylamino]-propyl}-2-methoxybenzenesulfonamide (formula I)

To a suspension of 5-{(2R)-2-[2-(2-ethoxy-phenoxy)ethylamino]-propyl}-2-methoxy-benzenesulfonic acid (3 g, 0.0073 mol) in dichloromethane and dimethylformamide in an inert atmosphere and cooled at 0° C./−5° C., was added 1.35 ml of thionyl chloride.

The resulting suspension was stirred at −5° C./0° C. until reaction is completed.

When reaction is completed the suspension was added to a mixture of water/ice and dichloromethane.

Organic phase is separated and evaporated, with vacuum, until oil was obtained.

To the oil obtained THF and ammonium was added and amination reaction takes place.

When reaction is completed water and dichloromethane was added and organic phase is separated.

Dichloromethane is evaporated with vacuum until oil is obtained and with the addition of an ethanolic hydrogen chloride solution tamsulosin hydrochloride precipitates.

The suspension was stirred for 1 hour at room temperature and the solid was filtered and dried.

After recrystallization from ethanol we obtain 5-{(2R)-2-[2-(2-ethoxy-phenoxy)-ethylamino]-propyl}-2-methoxy-benzenesulfonamide hydrochloride with a purity of 98.8% in area by HPLC. Chiral purity of the final product complies with the specification.

Tamsulosin optical purity and salts thereof are determined by HPLC on a chiral column.

The invention claimed is:

1. A process for producing 5-{(2R)-2-[2-(2-ethoxy-phenoxy)-ethylamino]-propyl}-2-methoxy-benzenesulfonamide of formula I

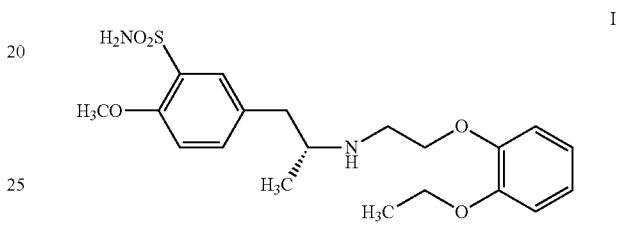

and pharmaceutically acceptable addition salts thereof, which process comprises the steps:

a) Reacting compound R,R-[2-(4-methoxy-phenyl)-1-methyl-ethyl]-(1-phenyl-ethyl)-amine of formula II or a salt thereof

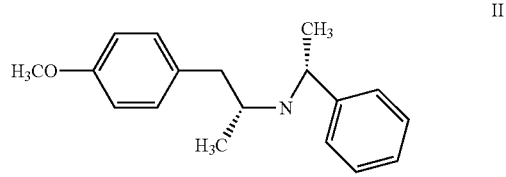

with chlorosulfonic acid with or without an organic solvent, to obtain compound R,R-2-methoxy-5-[2-(1-phenyl-ethylamino)-propyl]-benzenesulfonic acid of formula III

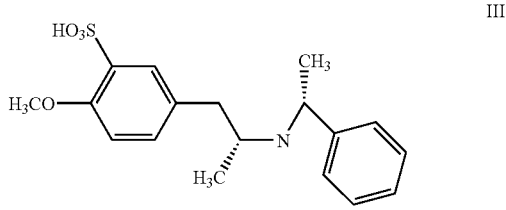

b) Hydrogenolysis of compound R,R-2-methoxy-5-[2-(1-phenyl-ethylamino)-propyl]-benzenesulfonic acid of formula III or a salt thereof carried out in an alcohol in the presence of a palladium catalyst using hydrogen or a source of hydrogen, to obtain compound R-(−)-5-(2-amino-propyl)-2-methoxy-benzenesulfonic acid of formula IV

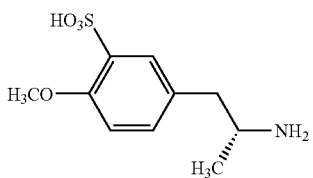

IV c) Reacting primary amine R-(−)-5-(2-amino-propyl)-2-methoxy-benzenesulfonic acid of formula IV, or a salt thereof, with a compound of formula V

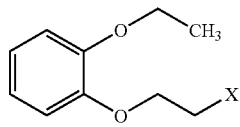

V wherein X represents an halogen atom selected from the group consisting of Cl; Br and I, to obtain 5-{(2R)-2-[2-(2-ethoxy-phenoxy)-ethylamino]-propyl}-2-methoxy-benzenesulfonic acid compound of formula VI

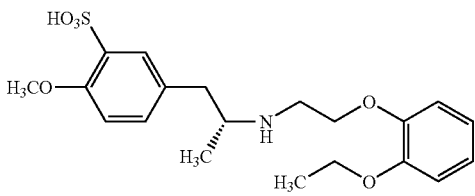

VI d) Reacting compound of formula VI with an halogenating agent, to obtain the corresponding sulfonylchloride of formula VII, and

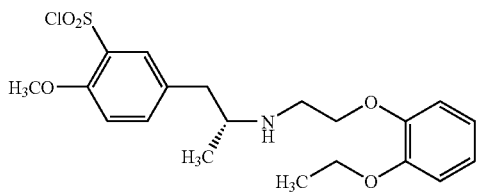

VII e) Reacting compound VII with ammonia to obtain compound I.

2. The process according to claim 1 wherein step (a) is carried out in an organic solvent, such as dichloromethane, monochlorobenzene or 1,2-dichloroethane.

3. The process according to claim 1 wherein the temperature of step (a) is from −30° C. to 10° C.

4. The process according to claim 1 wherein the temperature of step (a) is from −10° C. to 10° C.

5. The process according to claim 1 wherein the alcohol of step (b) is a lower alcohol of from 1 to 3 carbon atoms, such as ethanol or methanol.

6. The process according to claim 1 wherein the temperature of step (b) is from 30° C. to 60° C.

7. The process according to claim 1 wherein the temperature of step (b) is from 50° C. to 60° C.

8. The process according to claim 1 wherein the catalyst of step (b) is Pd/C.

9. The process according to claim 1 wherein the source of hydrogen in step (b) is ammonium formate, cyclohexene or sodium tetrahydroborate.

10. The process according to claim 1 wherein the reaction in step (c) is carried out in a solvent at a temperature of from 25° C. to 110° C.

11. The process according to claim 10 wherein the solvent is ethanol, DMF or water.

12. The process according to claim 10 wherein the temperature of step (c) is from 75° C. to 90° C.

13. The process according to claim 1 wherein the reaction in step (d) is carried out in an organic solvent at a temperature of from −30° C. to 0° C.

14. The process according to claim 13 wherein the organic solvent is DMF or a mixture of DMF and dichloromethane.

15. The process according to claim 13 wherein the temperature of step (d) is from −5° C. to 0° C.

16. The process according to claim 1 wherein the reaction of step (e) is carried out in an organic solvent at a temperature of 0° C. to 30° C.

17. The process according to claim 16 wherein the organic solvent is THF.

18. The process according to claim 16 wherein the temperature is from 15° C. to 25° C.

19. The process according to claim 1 wherein the organic solvent of step (a) is dichloromethane, monochlorobenzene or 1,2-dichloroethane; the alcohol of step (b) is ethanol or methanol and the catalyst is Pd/C; step (c) is carried out in a solvent which is ethanol, DMF or water; step (d) is carried out in an organic solvent which is DMF or a mixture of DMF and dichloromethane; and step (e) is carried out in an organic solvent which is THF.

20. The process according to claim 19 wherein step (a) is carried out at a temperature of from −10° C. to 10° C.; step (b) is carried out at a temperature of from 50° C. to 60° C.; step (c) is carried out at a temperature of from 75° C. to 90° C.; step (d) is carried out at a temperature of from −10° C. to 0° C.; and step (e) is carried out at a temperature of from 15° C. to 25° C.

21. The process according to claim 20 wherein the organic solvent of step (a) is dichloromethane.

22. R,R-2-methoxy-5-[2-(1-phenyl-ethylamino)-propyl]-benzenesulfonic acid of formula III

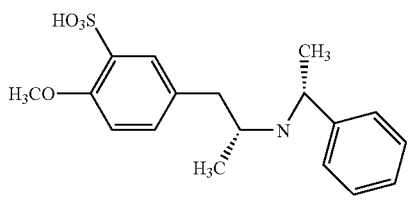

III or an addition salt thereof.

* * * * *